(12) United States Patent
McCoy et al.

(10) Patent No.: US 9,480,412 B1
(45) Date of Patent: Nov. 1, 2016

(54) DISPOSABLE ELECTRODE ASSEMBLY

(71) Applicant: Rhythmlink International, LLC, Columbia, SC (US)

(72) Inventors: Daniel E. McCoy, Murrells Inlet, SC (US); Shawn V. Regan, Columbia, SC (US); William Webb, Huntersville, NC (US)

(73) Assignee: Rhythmlink International LLC, Columbia, SC (US)

(*) Notice: Subject to any disclaimer, the term of this patent is extended or adjusted under 35 U.S.C. 154(b) by 246 days.

(21) Appl. No.: 14/465,204

(22) Filed: Aug. 21, 2014

Related U.S. Application Data (60) Provisional application No. 61/868,317, filed on Aug. 21, 2013.

(51) Int. Cl.
*A61B 5/0478* (2006.01)
*A61B 5/00* (2006.01)
*A61B 5/04* (2006.01)

(52) U.S. Cl.
CPC ......... *A61B 5/0478* (2013.01); *A61B 5/04001* (2013.01); *A61B 5/6814* (2013.01)

(58) Field of Classification Search
CPC    A61B 5/04001; A61B 5/0408; A61B 5/042; A61B 5/0478; A61B 5/0492; A61B 5/04025
USPC .................. 600/372, 373, 382, 383, 386
See application file for complete search history.

(56) References Cited

U.S. PATENT DOCUMENTS

| | | | | |
|---|---|---|---|---|
| 2,782,786 | A * | 2/1957 | Krasno | A61B 5/04082 252/519.4 |
| 4,155,353 | A * | 5/1979 | Rea | A61B 5/04 600/380 |
| 4,311,152 | A * | 1/1982 | Modes | A61B 5/04025 600/392 |
| 5,361,760 | A * | 11/1994 | Normann | A61B 5/04001 600/377 |
| 8,694,070 | B2 | 4/2014 | Wilson | |

* cited by examiner

*Primary Examiner* — Lee S Cohen
(74) *Attorney, Agent, or Firm* — Michael A. Mann; Nexsen Pruet, LLC

(57) ABSTRACT

An electrode assembly includes a handle, holder, and electrode with an electrical conductor. The electrode is loaded into the holder with its attached conductor. The holder includes a protective cap, a resilient button with a flange, an alignment ring, two plungers each with a spring, and a retention ring. The flange and retention ring both have plural holes in registration and with posts depending from the alignment ring in order to hold the retention ring in place. Inside the button are two plungers, one on top of the other, and each with its own spring resisting downward pressure. Once the cap is removed from the button, the holder is placed against the skin of a patient, and the button is pressed, the top plunger pushes the bottom plunger against the skin of the patient and then the electrode from the protection ring, thereby ejecting the electrode.

20 Claims, 8 Drawing Sheets

DISPOSABLE ELECTRODE ASSEMBLY

PRIORITY CLAIM

Claim is made to the priority benefit of U.S. provisional patent application Ser. No. 61/868,317, filed Aug. 21, 2013, which is hereby incorporated in its entirety by reference.

BACKGROUND OF THE INVENTION

In neurological monitoring, electrodes are attached to the scalp of the patient and connected via electrical conductors to neurological monitoring equipment. Various types of electrodes may be chosen for use. In some instances, when the patient may also be subject to magnetic resonance imaging (MRI) and computerized tomography (CT) testing in addition to neurological monitoring, very small electrodes, such as those manufactured by Persyst Development Corporation and sold under the trademark PRESS-ON, are attached to the scalp and, because of their small size, may be left in place during the MRI and/or CT testing. These electrodes are resilient so that they may be easily deformed for insertion into an applicator and, when the applicator is applied to the skin of a patent and the electrode is ejected, the electrode springs resiliently back into its original configuration and, on so doing, self-inserts laterally into the skin of the patient. Such an electrode may be applied by an applicator such as that shown and described in U.S. Pat. No. 8,694,070 B2, which is incorporated herein in its entirety by reference.

SUMMARY OF THE INVENTION

According to its major aspects and briefly recited, the present invention is an electrode assembly that includes a handle and a holder for an electrode. The electrode is loaded into the holder by deforming it for insertion and then threading its attached electrical conductor through a channel in the holder and then along the handle and through one or more catches carried by the handle for managing the conductor and for preventing a sudden tension on the conductor from detaching it from the electrode. The holder facilitates ejection of the electrode into the skin of the patient using a double plunger system, first to move the electrode into contact with the patient's skin and only then to eject it. The present electrode system is simple enough to be easily manufactured for one time use. The electrode system is also designed to be easily integrated and attached to electrode management systems such as electrode templates and electrode headsets.

BRIEF DESCRIPTION OF THE DRAWINGS

In the figures.

DETAILED DESCRIPTION OF THE EMBODIMENTS OF THE INVENTION

The present invention is an electrode assembly for use in attaching an electrode to the epidermis of a patient's skin. The electrode is used in neurological monitoring, such as in obtaining electrical signals for electroencephalographs, and will be connected to the skin of the patient and, via an electrical conductor, to monitoring equipment for delivering electrical signals detected by the electrode from the patient's brain.

Figure 5:
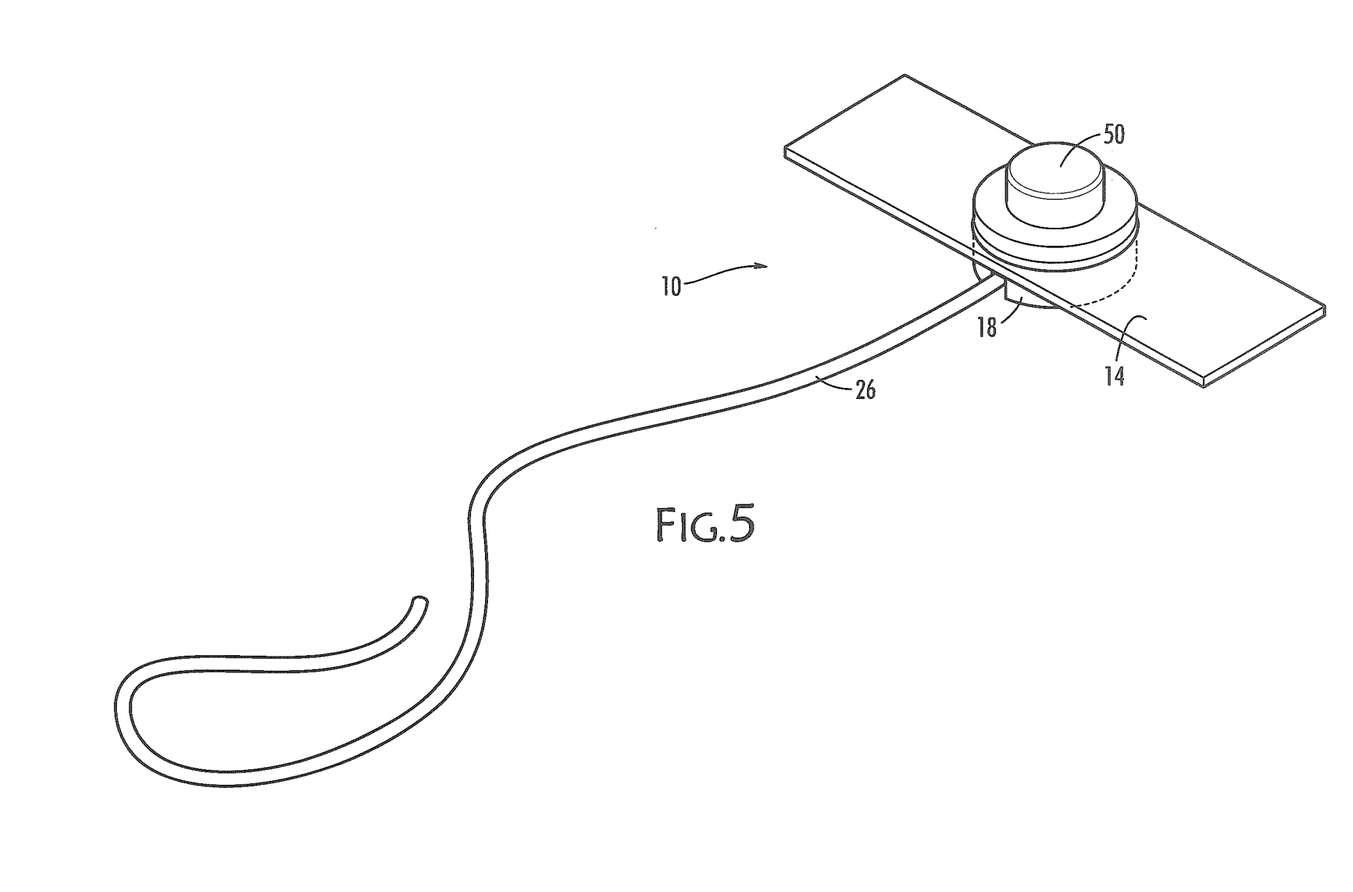
FIG. 5 is a top perspective view of an alternate embodiment of an electrode assembly without the protective cap on the holder, according to an embodiment of the present invention.

As shown in FIGS. 1-7, the disposable electrode assembly 10 includes a handle 14 that carries an electrode holder 18. Handle 14 has a major axis parallel to its long dimension. Holder 18 has a major axis perpendicular to handle 14. The major axis of handle 14 may intersect the axis of holder 18, as shown in FIGS. 1-4 or the axis of holder 18 may bisect handle 14 as shown in the embodiment of FIG. 5. Holder 18 holds an electrode 22 (FIGS. 2-4, 6-8) securely until it is ejected from holder 18 into the skin of the patient, the mechanism for which ejection will be described presently.

The present electrode assembly may be integrated with a headset or template. Handle 14 may be attached to a headset or template by gluing, fitting, welding, sewing, or other convenient means.

Electrode 22 is of the type that is made of a resilient electrical conductor, such as spring steel, so that it functions both as an electrode for neurological monitoring and as a resiliently deformable electrode so that it can be deformed to fit into a recess 24 in holder 18, which is an area of smaller diameter than the diameter of electrode 22. When the deformed electrode 22 is ejected from recess 24, it springs resiliently to its configuration prior to deformation.

Figure 3:
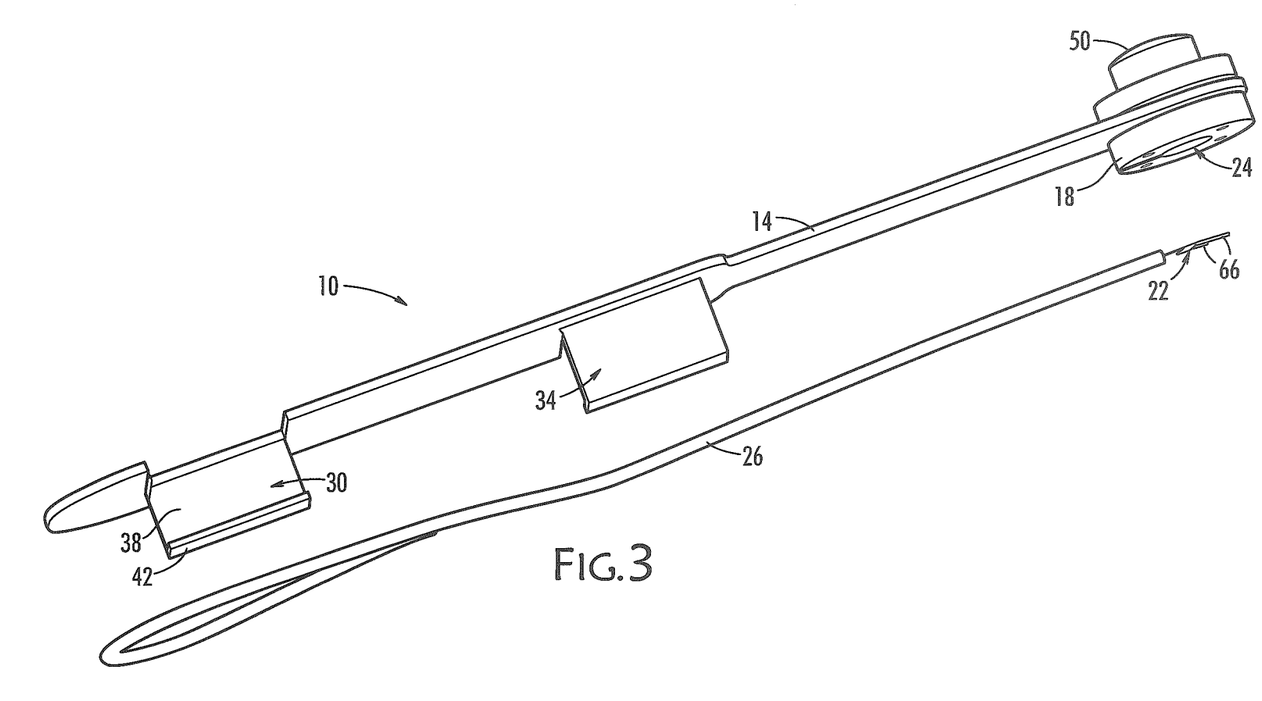
FIG. 3 is a side perspective view of the electrode assembly with the protective cap removed and the electrode ejected from the holder, according to an embodiment of the invention.
Figure 4:
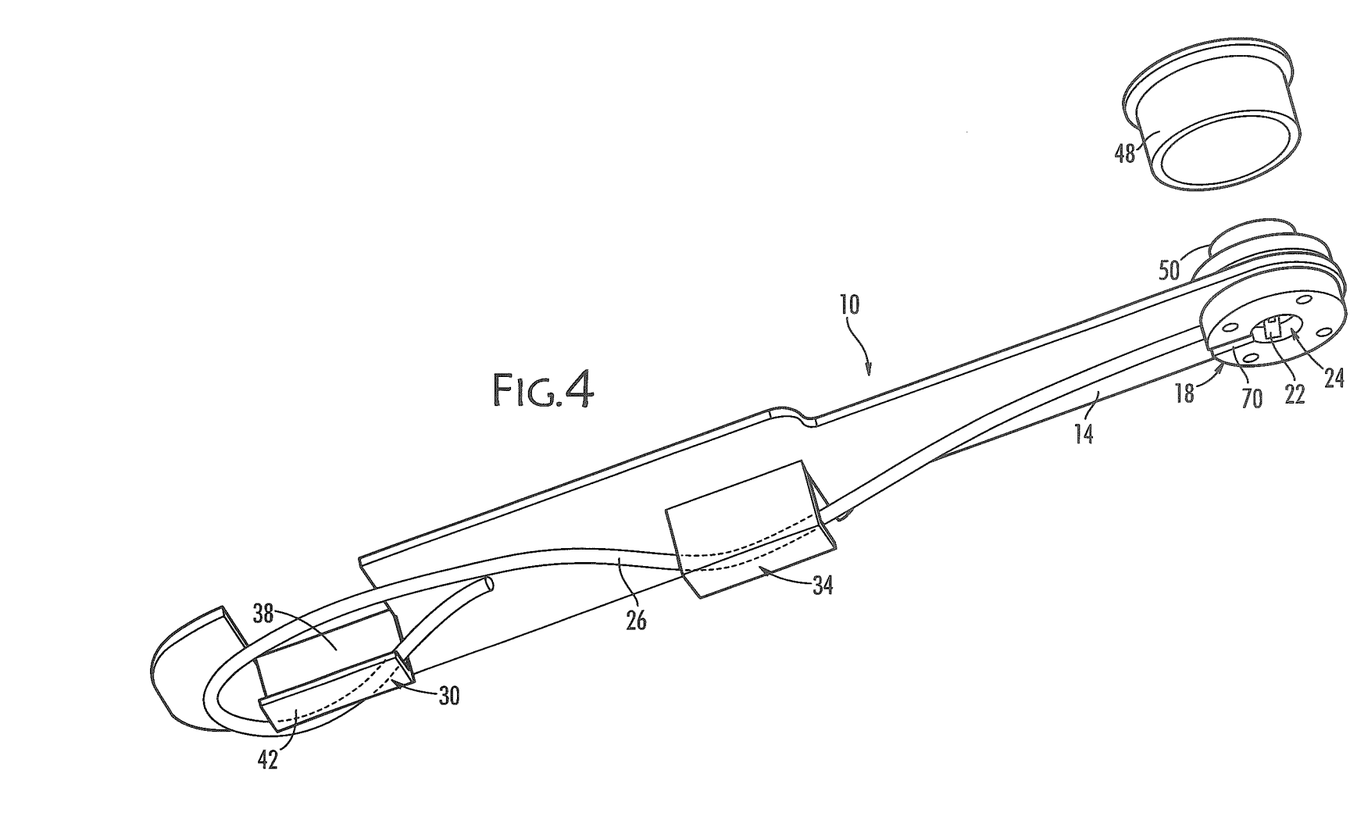
FIG. 4 is a bottom perspective view of the electrode assembly with the protective cap removed from the holder, according to an embodiment of the present invention.
Figure 6:
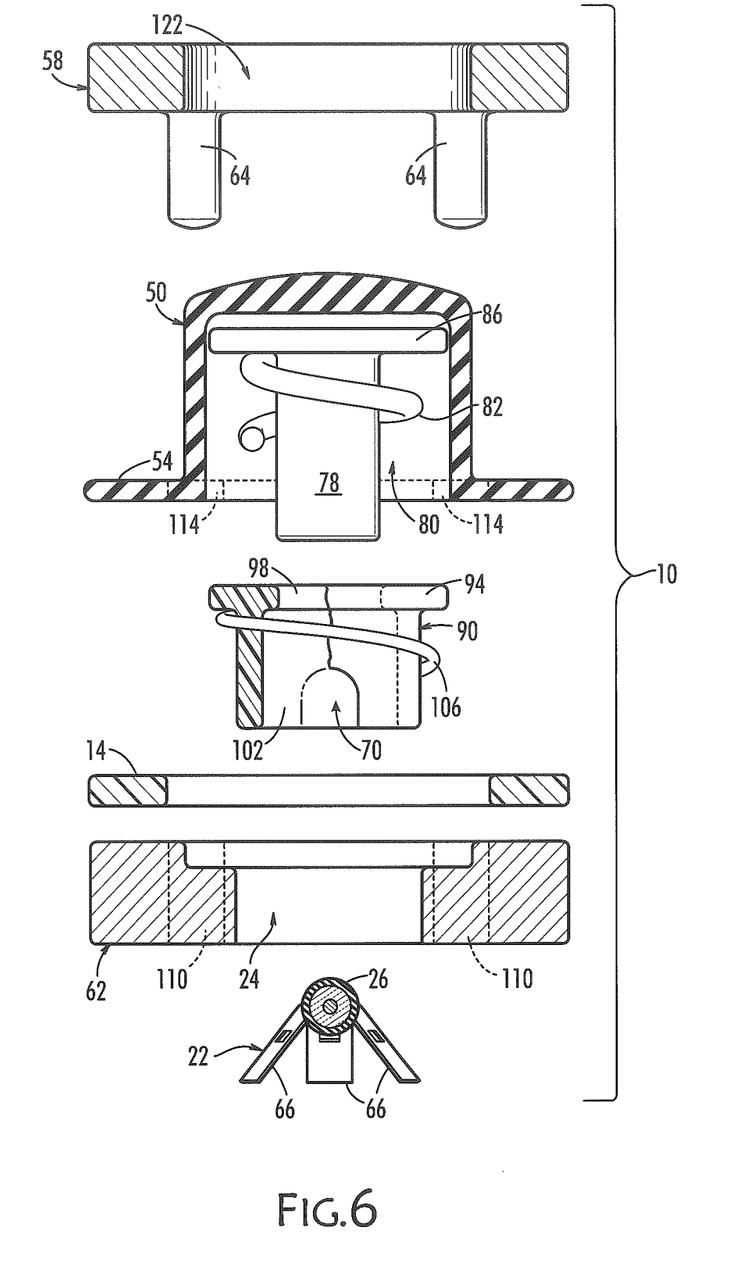
FIG. 6 is a cross sectional, exploded view of the electrode assembly, according to an embodiment of the present invention.
Figure 7:
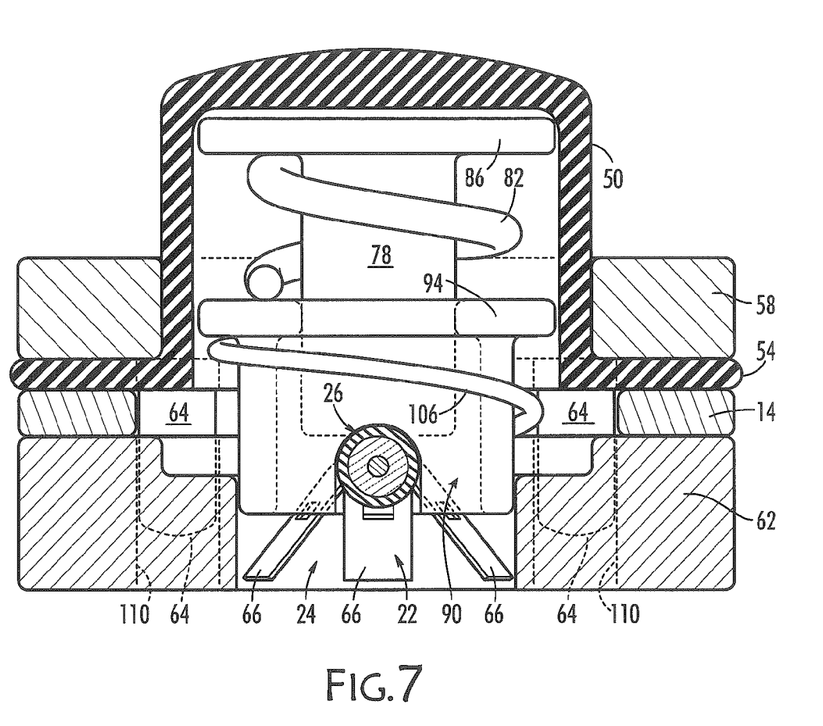
FIG. 7 is a cross-sectional view of the assembled electrode assembly, according to an embodiment of the present invention.
Figure 8:
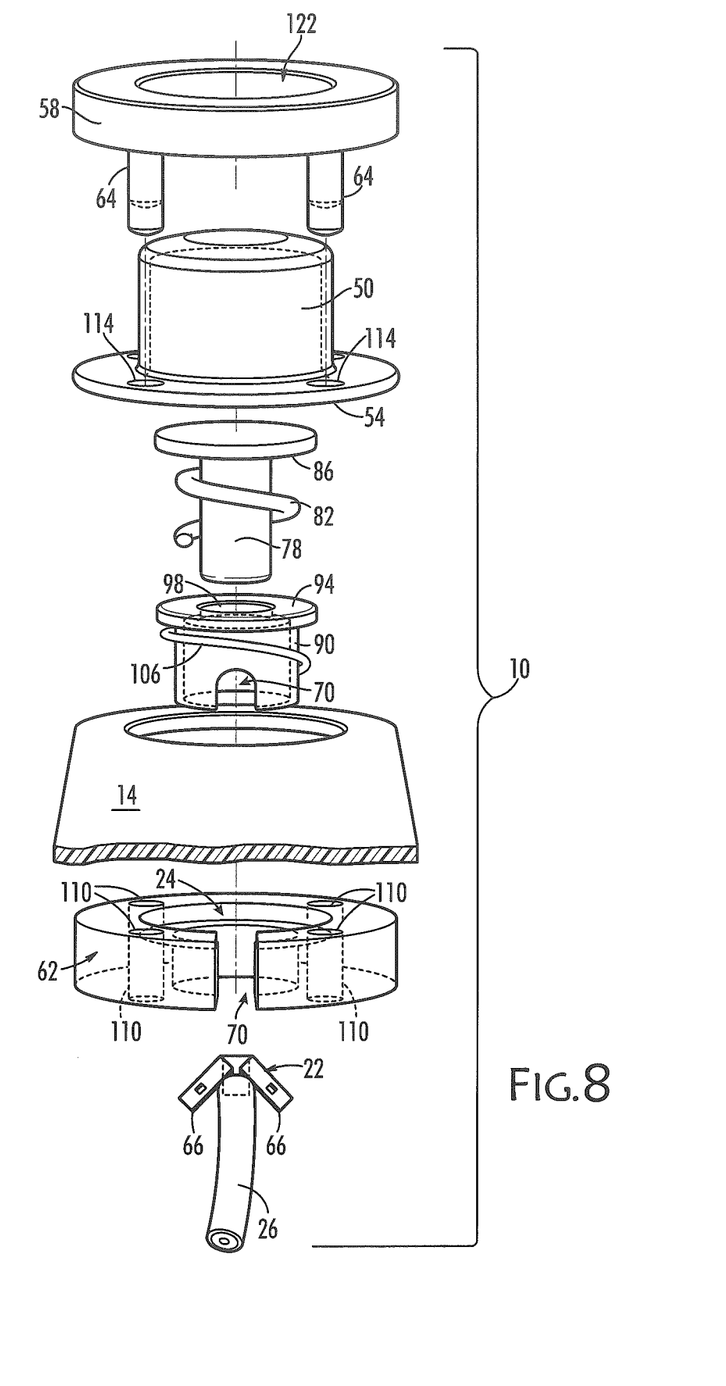
FIG. 8 is a side perspective, exploded view of the electrode assembly, according to an embodiment of the present invention.

Electrode 22 may have plural legs 66, best seen in FIGS. 6-8, that arch toward an axis through the center of electrode 22 from an initial orientation more perpendicular to that axis under an external, deforming force (see FIG. 3). Electrode 22 is connected, by, for example, soldering, to an electrical conductor 26, which may be an insulated metal wire. The distal end of electrical conductor 26 may be terminated with any convenient end fitting for use with the particular monitoring equipment, such as a plug or jack (not shown) but as will be configured to be receivable by the particular monitoring equipment.

Handle 14 may have one or more catches 30, 34. A catch is defined herein as a static structure used to impose a frictional force on the conductor 26 with respect to the direction of its movement but to which the conductor 26 is not secured or tied. A catch therefore uses friction to slow movement of electrical conductor 26 when it is pulled parallel to its long dimension, and allows slack in the length of conductor 26 to be taken up.

Catches 30, 34, also help to manage conductor 26. Management of conductor 26 means that catches 30, 34, help keep conductor 26 aligned with handle 14 so that both may be held easily with one hand by the user. Catches 30, 34, thus tend to manage and to protect electrical conductor 26 by preventing or reducing tension on it, particularly in reducing the acceleration of tension that, when applied to the connection between electrode 22 and electrical conductor 26 may cause the connection to break. Catches 30, 34 also help manage electrical conductor 26 by preventing tangling and knotting of conductor 26.

Figure 1:
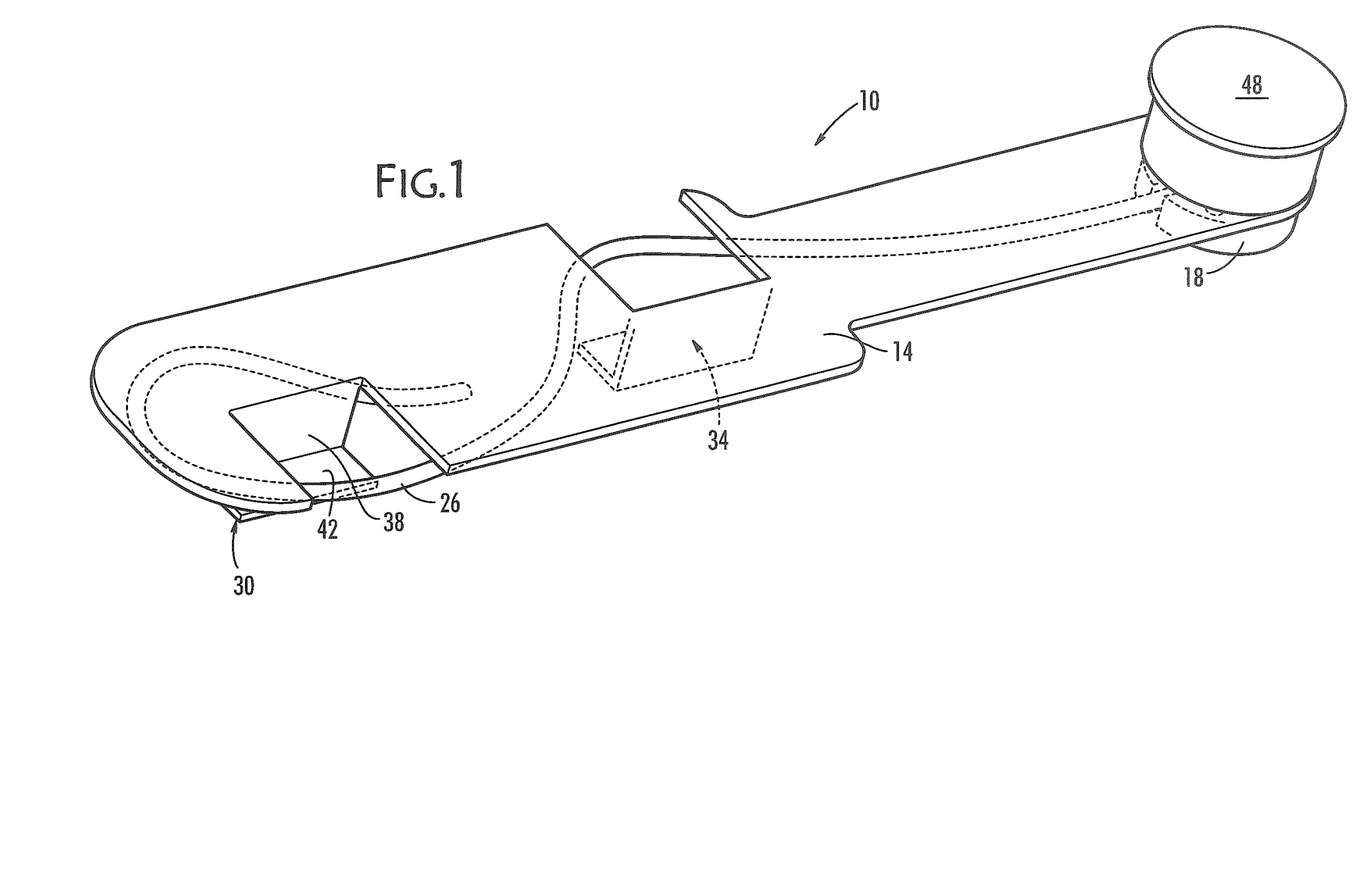
FIG. 1 is a top perspective view of the present disposable electrode assembly, according to an embodiment of the invention.
Figure 2:
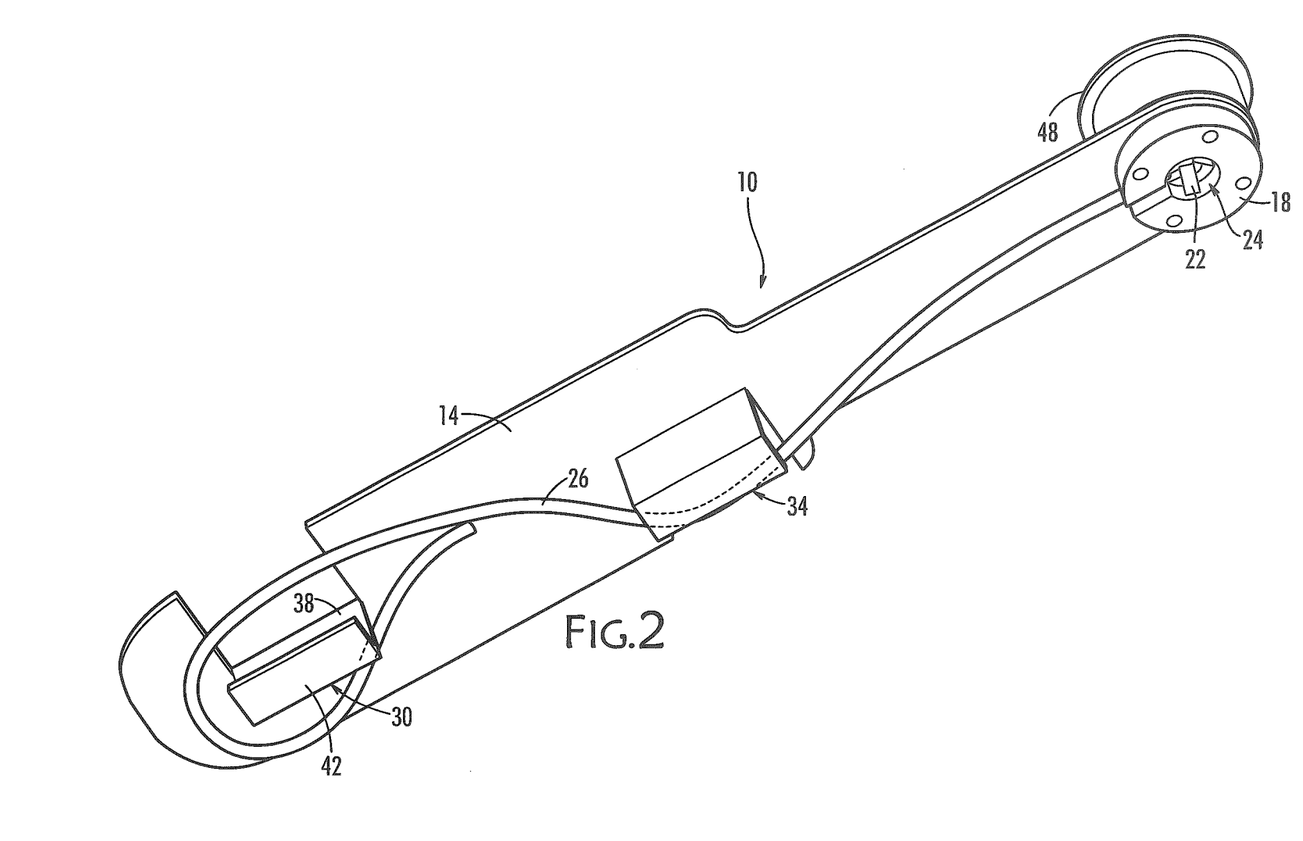
FIG. 2 is a bottom perspective view of the holder of the electrode assembly, according to an embodiment of the invention.

Catches 30, 34 may be conveniently formed integrally from handle, for example, by cutting and bending portions of handle 14 to extend above the plane of handle 14 and around which electrical conductor 26 may be threaded, as seen in FIG. 2. For example, catch 30 may be formed by making a pair of transverse slits in handle 14 and bending the area between the slits to form a flap having a first panel 38 and a second panel 42. First panel 38 thus provides a barrier perpendicular to the plane of handle 14 to hold electrical conductor 26 away from the major axis of handle 14 in order to cause a change in direction of conductor 26, and then a second panel 42 parallel to the plane of handle 14, to provide a barrier to help hold electrical conductor 26 close to handle 14. Catches 30, 34, may be on the same side of handle 14, but formed from opposing edges, as shown, to establish at least two sequential directional changes in the path to be taken by electrical conductor for generating frictional forces between catches 30, 34, and electrical conductor 26 when responding to changes in tension on electrical conductor 26.

Electrode holder 18 includes several components, best seen in FIG. 6-8. FIGS. 6 and 8 show exploded views of holder 18; FIG. 7 shows an assembled, cross-sectional view of holder 18 with an electrode 22 loaded inside and not visible externally. Holder 18 includes protective cap 48 over a button 50 with a flange 54, an alignment ring 58, and a retention ring 62 that protects electrode 22. Button 50 is preferably made of a resilient material such as rubber or soft plastic. Protective cap 48 prevents the accidental pressing of button 50 and is simply a friction fitted cap over button 50. Alignment ring 58 helps to align button 50 and retention ring 62 as will be explained below. Retention ring 62 prevents legs 66 of electrode 22 from being exposed prior to ejection.

FIGS. 6-8 shows the bottom of holder 18 where electrode 22 is clearly visible with its legs 66. Electrical conductor 26 is also visible, running through a channel 70 (best seen in FIGS. 4 and 8) formed in retention ring 62.

Electrode 22 is deformed when seated in holder 18 by bending the distal ends of its legs 66 toward each other and inserting electrode 22 into recess 24 of holder 18, as will be described presently.

FIG. 3 shows the ejected electrode 22 with its electrical connector 26 from holder 18 when button 50 is pressed. Through the interior mechanism of holder 18, pressing button 50 against an unmoving surface, such as when retention ring 62 is pressed against the skin of a patient, causes electrode 22 to be ejected from holder 18, whereupon its legs 66 spring resiliently from the bent configuration to the deployed configuration where they are splayed.

FIGS. 6 and 8 show an exploded view of holder 18. Button 50 receives a first plunger 78 in its interior 80. A first spring 82 having a first spring force engages a top flange 86 of first plunger 78. A second plunger 90, also with a top flange 94 but with a hole 98 formed in top flange 94, is received in interior 80 of button 50, so that first plunger 78 penetrates through hole 98 of top flange 94. Second plunger 90 has a hollow interior 102 that will receive electrode 22 when electrode 22 is loaded into holder 18.

Second plunger 90 has a second spring 106 with a different spring force. Both first and second springs 82, 106, resist pressure on button 50 but the first spring force of first spring 82 is greater than the second spring force of second spring 106 so that force on button 50 first presses second plunger 90 down and then, when the resistance against further movement of second plunger 90 has increased sufficiently, first plunger 78 will be moved against the first spring force of first spring 82, until electrode 22 is ejected from holder 18.

Retention ring 62 of holder 18 protects legs 66 of electrode 22 and also has plural circular holes 110 formed therein, each of which has an axis parallel to that of first and second plungers 78, 90. Flange 54 of button 50 also has plural circular holes 114 that may be placed in registration with holes 110 of retention ring 62. An alignment ring 118 having a central hole 122 surrounds button 50 and carries plural depending posts 64 that are axially aligned, dimensioned and deployed to fit into holes 110 and 114 thereby aligning and maintaining the alignment of button 50, including its flange 54, and retention ring 62 before, after and during operation to release electrode 22.

In operation, an electrode 22 may be loaded into interior 102 of second plunger 90 so that its electrical conductor 26 extends through channel 70 in retention ring 62 and thence through catches 30, 34, formed in handle 14. Holder 18 is then positioned with retention ring 62 against the skin of a patient. The user next applies steady pressure on button 50 of holder 18 against first and second springs 82, 106, respectively. Second spring 106, with a smaller spring force than that of first spring 82, compresses more readily than first spring 82. When top flange 94 of second plunger 90 reaches the end of its travel, continued pressure on button 50 no longer compresses second spring but begins to compresses first spring 82, thereby moving first plunger 78 toward retention ring 62. When first plunger 78 travels sufficiently far inside of second plunger 90, it reaches central body 74 of electrode 22 and expels electrode 22 from holder 18.

Those skilled in the art of neurological monitoring and electrodes therefor will understand that many changes and substitutions may be made in the foregoing description of embodiments of the invention without departing from the spirit and scope of the present invention, which is defined by the appended claims.

The invention claimed is:

1. An electrode assembly for use in applying an electrode to the skin of a patient, said assembly comprising:
   (a) a handle;
   (b) a holder attached to said handle, said holder having a top, an opposing bottom and an exterior, said holder having a recess and a channel formed in said bottom of said holder, said channel running from said recess to said exterior of said holder;
   (c) an electrode carried within said recess by said holder;
   (d) an electrical conductor carried in said channel and attached to said electrode; and
   (e) a button carried by said holder so that, when said holder is placed in engagement with the skin of a patient and said button of said holder pressed, said holder ejects said electrode from said recess into the skin of said patient.

2. The electrode assembly of claim 1, wherein said handle carries a first catch through which said electrical conductor is threaded to provide slack in said electrical conductor and hold said electrical conductor to said handle.

3. The electrode assembly of claim 2, wherein said first catch is integrally formed of said handle.

4. The electrode assembly of claim 2, wherein said handle carries a second catch.

5. The electrode assembly of claim 4, wherein said handle has a first side and an opposing second side, and wherein said first catch and said second catch are carried on said first side of said handle.

6. The electrode assembly of claim 4, wherein said handle has a first edge and an opposing second edge, and wherein said first and said second catches are on said first and said second edges, respectively.

7. The electrode assembly of claim 1 wherein said holder has an axis and said handle has a major dimension, and wherein said major dimension of said handle bisects said axis of said holder.

8. The electrode assembly of claim 7, wherein said axis of said holder bisects said handle.

9. The electrode assembly as recited in claim 1, wherein said holder further comprises a first plunger and a second plunger, said first and said second plungers being coaxial so that, when said button is pressed, said first and said second plungers move in the same direction.

10. The electrode assembly as recited in claim 9, wherein said second plunger carries said electrode and wherein said second plunger is hollow so that said first plunger moves through said second plunger to eject said electrode from said holder.

11. The electrode assembly as recited in claim 9, further comprising a first spring resisting movement of said first plunger and a second spring resisting movement of said second plunger, and wherein a spring force of said first spring is greater than a spring force of said second spring.

12. The electrode assembly as recited in claim 11, wherein said second plunger moves said electrode into engagement with the skin of said patient before said first plunger ejects said electrode from said second plunger.

13. The electrode assembly as recited in claim 9, wherein said holder further comprises a retention ring positioned between said button and the skin of said patient when said holder is placed against the skin of said patient.

14. The electrode assembly as recited in claim 13, wherein said retention ring has a central hole through which said electrode is ejected from said second plunger by said first plunger into the skin of said patient.

15. The electrode assembly as recited in claim 1, further comprising an alignment ring, said alignment ring having four depending posts, said button having a flange with four holes formed therein, said posts of said alignment ring being in registration with said holes in said flange of said button so that said posts of said retention ring are received in said holes in said flange.

16. The electrode assembly as recited in claim 1, further comprising a retention cover, said retention cover fitting over said button to prevent said button from being pressed prematurely.

17. An electrode assembly for use in applying an electrode to the skin of a patient, said assembly comprising:
 (a) a holder having a top, an opposing bottom and an exterior, said holder having a recess and a channel formed in said bottom of said holder, said channel running from said recess to said exterior of said holder;
 (b) an electrode carried within said recess by said holder;
 (c) an electrical conductor carried in said channel and attached to said electrode; and
 (d) a button carried by said holder so that, when said holder is placed in engagement with the skin of a patient and said button of said holder pressed, said holder ejects said electrode from said recess into the skin of said patient.

18. The electrode assembly as recited in claim 17, wherein said holder further comprises a retention ring positioned between said button and the skin of said patient when said holder is placed against the skin of said patient.

19. The electrode assembly as recited in claim 18, wherein said holder further comprises a first plunger and a second plunger, said first and second plungers being coaxial so that, when said button is pressed, said first and second plungers move in the same direction and wherein said retention ring has a central hole through which said electrode is ejected from said second plunger by said first plunger into the skin of said patient.

20. The electrode assembly as recited in claim 17, further comprising a retention cover, said retention cover fitting over said button to prevent said button from being pressed prematurely.

* * * * *